United States Patent [19]
Watanuki et al.

[11] Patent Number: 5,210,250
[45] Date of Patent: May 11, 1993

[54] METHOD FOR DECOLORIZING PURIFICATION OF HALOGENATED SILANE

[75] Inventors: Isao Watanuki; Hiroshi Tsumura; Nobuhiko Kodana, all of Gunma; Kazushi Satoh, Tokyo; Masanori Fukuhira; Hidehiko Aonuma, both of Gunma, all of Japan

[73] Assignee: Shin-Etsu Chemical Co. Ltd., Tokyo, Japan

[21] Appl. No.: 935,797

[22] Filed: Aug. 27, 1992

[30] Foreign Application Priority Data

Aug. 28, 1991 [JP] Japan .................................. 3-242624

[51] Int. Cl.$^5$ ............................................. C07F 7/08
[52] U.S. Cl. ...................................... 556/466; 423/342
[58] Field of Search ........................ 556/466; 423/342

[56] References Cited

U.S. PATENT DOCUMENTS

| | | | |
|---|---|---|---|
| 3,414,603 | 12/1968 | Malavsky | 556/466 |
| 3,801,615 | 4/1976 | Chuang | 556/466 X |
| 4,661,612 | 4/1987 | George et al. | 556/466 X |
| 5,138,081 | 8/1992 | De Vries et al. | 556/466 |

*Primary Examiner*—Paul F. Shaver
*Attorney, Agent, or Firm*—Millen, White, Zelano & Branigan

[57] ABSTRACT

A simple but very effective and reliable method is proposed for the decolorizing purification of a halogenated silane compound, e.g., methyl trichlorosilane, colored by containing a very small amount of heavy metal impurities such as iron. The method comprises: contacting the halogenated silane compound with a small amount of a cationic surface active agent which is solid and insoluble in the silane such as a quaternary ammonium salt, e.g., trimethyl octadecyl ammonium chloride, for 2 to 240 minutes; and then separating the silane compound from the cationic surface active agent.

11 Claims, No Drawings

METHOD FOR DECOLORIZING PURIFICATION OF HALOGENATED SILANE

BACKGROUND OF THE INVENTION

The present invention relates to a method for the decolorizing purification of a halogenated silane compound or, more particularly, to a method for the decolorizing purification of a liquid halogenated silane compound such as methyl trichlorosilane, vinyl trichlorosilane and the like useful, for example, as a starting material in the synthesis of an oxime group-containing organosilane compound.

Halogenated silane compounds in general are useful as a starting material for the synthetic preparation of various kinds of organosilicon compounds or, in particular, silicone compounds. A serious problem in the use of a halogenated silane compound as a starting material organosilicon compounds is that the halogenated silane compound is sometimes colored due to the trace content of various kinds of coloring heavy metals so as to greatly decrease the commercial value of the organosilicon compound as the product therefrom due to unavoidable coloration. This problem is particularly important when the silicone product produced from the halogenated silane compound is used in an application to colorless or white materials such as fibrous materials or in the preparation of silicone rubbers of transparency formulation. In this regard, it is eagerly desired to develop a simple and reliable method for the decolorizing purification of an organochlorosilane used as a starting material for an oxime group-containing organosilicon compound. Colored silane compounds can of course be decolorized and purified by distillation but this procedure is relatively expensive resulting in an increase of the production cost. Further, the coloring impurities in a halogenated silane compound can be removed by using active carbon but the efficiency of this method is relatively low and far from satisfactory.

Oximesilane compounds are prepared usually by the reaction of an organochlorosilane such as methyl trichlorosilane with a stoichiometric amount of an oxime compound such as methyl ethyl ketoxime in the presence of a stoichiometric amount of an organic base as an acceptor of hydrogen chloride formed as a by-product of the dehydrochlorination reaction as is disclosed in Japanese Patent Publication 39-29837. On the other hand, Japanese Patent Publication 1-21834 discloses a method in which the reaction of an organochlorosilane and an oxime compound is conducted by using the oxime compound in an amount of twice of the stoichiometric amount so that the excess of the oxime compound serves as the acid acceptor. Alternatively, Japanese Patent Kokai 63-227592 discloses a preparation method of an oximesilane compound in which an organochlorosilane compound is reacted with a stoichiometric amount of an oxime compound under continuous blowing of ammonia gas into the reaction mixture in an amount of 1.04 to 1.46 times of the stoichiometric amount to serve as the acid acceptor.

The oximesilane compound prepared by the above described method is always more or less colored in brown or green due to the presence of a few ppm of a compound of heavy metals such as iron, chromium, nickel, manganese and the like in the form of $FeCl_3$, $CrCl_3$, $NiCl_2$ and $MnCl_2$. Complete prevention of coloration of an oximesilane compound thereby is a very difficult matter from the economical standpoint despite the countermeasures thus far undertaken including purification of the starting materials, appropriate selection of the material of the reaction vessels and so on in so far as the halogenated silane compound as the starting material thereof is contaminated with a few ppm of these heavy metal compounds.

Similar difficulties are encountered relative to halogenated silane compounds due to contamination with heavy metals to cause coloration of the silane compound in yellow to brown. Even when a halogenated silane compound is purified by distillation to completely remove heavy metal impurities, such a purified and colorless halogenated silane compound is already contaminated when it is used as a starting material in the next step because of the many chances by which a heavy metal impurity is taken into the silane compound by contacting with pipe lines, storage vessels and the like.

SUMMARY OF THE INVENTION

The present invention accordingly has an object to provide a simple and reliable method for the decolorization purification of a liquid halogenated silane compound such as organochlorosilanes.

Thus, the present invention provides a decolorizing purification of a halogenated silane compound, which is liquid at room temperature, represented by the general formula $R^1_{4-a}SiX_a$, in which X is an atom of halogen such as chlorine, $R^1$ is a hydrogen atom or a monovalent hydrocarbon group selected from the class consisting of alkyl groups, alkenyl groups, aryl groups, aralkyl groups and cycloalkyl groups as well as halogen-substituted monovalent hydrocarbon groups and the subscript a is 1, 2, 3 or 4, which method comprises the steps of: (a) bringing the halogenated silane compound into contact with a cationic surface active agent which is solid at room temperature and insoluble in the halogenated silane compound; and (b) separating the halogenated silane compound from the cationic surface active agent.

DETAILED DESCRIPTION OF THE PREFERRED EMBODIMENTS

The objective material of the inventive method is a halogenated silane compound or, in particular, chlorinated silane compound, which is liquid at room temperature, represented by the general formula $R^1_{4-a}SiX_a$, in which each symbol has the meaning as defined above. Examples of the organochlorosilane compound suitable for the treatment according to the inventive method include; tetrachlorosilane, trimethyl chlorosilane, dimethyl dichlorosilane, methyl trichlorosilane, methyl ethyl dichlorosilane, ethyl trichlorosilane, diethyl dichlorosilane, triethyl chlorosilane, n-propyl trichlorosilane, isopropyl trichlorosilane, 2-chloroethyl trichlorosilane, 3-chloropropyl trichlorosilane, vinyl trichlorosilane, vinyl methyl dichlorosilane, propenyl trichlorosilane, allyl trichlorosilane, phenyl trichlorosilane, benzyl trichlorosilane and the like. Among the above named chlorinated silane compounds, the inventive method is particularly effective for the compound having, in a molecule, at least one organic group denoted by $R^1$ in the above given general formula which is a methyl, ethyl or vinyl group.

Several classes of cationic surface active agents are suitable for use in the inventive method to be brought into contact with the halogenated silane compound.

Examples of the suitable classes include a salt of a protonated amine such as $RN^+H_3$, $R_2N^+H_2$ and $R_3N^+H$; protonated quaternary ammonium salts; salts of a protonated carboxylic acid such as $RC^+(OH)_2$; salts of a protonated nitrile such as $RCN^+H$; salts of a protonated sulfoxide such as $R_2S^+OH$; salts of a protonated mercaptan such as $RS^+H_2$; quaternary phosphonium salts; and salts of a protonated phosphine such as $R_3P^+H$, in which R is a hydrogen atom or a monovalent hydrocarbon group. The cationic part of each of the above named salts should have from 5 to 80 or, preferably, from 6 to 30 carbon atoms. The counteranion to couple with the cationic part of the salt is selected from halogen to couple with the cationic part of the salt is selected from halogen ions, sulfate ion and phosphate ion or, preferably a chlorine ion. When 2 or more of the groups R are contained in a molecule of the surface active agent, they can be of the same kind or different kinds from each other. These cationic surface active agents can be used either singly or as a combination of two kinds or more according to need.

Among the above named classes of the cationic surface active agents, quaternary ammonium salts are preferred in the inventive method. Particular examples of the cationic surface active agent in the form of a quaternary ammonium salt include; tetra(n-butyl) ammonium chloride; tetra(n-hexyl) ammonium chloride; tetra(n-heptyl) ammonium chloride; trimethyl n-nonyl ammonium chloride; tri(n-octyl) n-propyl ammonium chloride; n-cetyl trimethyl ammonium chloride; trimethyl octadecyl ammonium chloride and the like, of which the last mentioned trimethyl octadecyl ammonium chloride is the most preferable.

As is mentioned before, it is essential that the cationic surface active agent is solid at room temperature and substantially insoluble in the halogenated silane compound because, if the cationic surface active agent is dissolved in the silane compound, the silane compound must be again subjected to a purification process to remove the dissolved cationic surface active agent. In this regard, cationic surface active agents of several classes cannot be used for the purpose including ethyl ammonium chloride, trimethyl ammonium chloride, protonated acetonitrile chloride, protonated acetic acid chloride and the like.

The amount of the cationic surface active agent to be brought into contact with the halogenated silane compound is usually in the range from 0.001% to 10% by weight based on the halogenated silane compound though dependent on the degree of contamination of the silane compound with heavy metals. The most simple way for bringing the silane compound into contact with the cationic surface active agent is to add the cationic surface active agent to the silane compound and to agitate or shake the mixture to cause a flow of the silane compound for 2 to 240 minutes at a temperature of $-5°$ to 40° C. or, preferably, 10° to 35° C. Thereafter, the mixture is subjected to a suitable treatment for solid-liquid separation such as filtration, centrifugal separation and the like in order to separate the cationic surface active agent from the silane compound. It is of course possible to continuously conduct the contacting between the silane compound and the cationic surface active agent by passing down the liquid silane compound through a fixed bed formed by filling a column with the cationic surface active agent in a granular form to be percolated therethrough.

In the following, the method of the invention is illustrated in more detail by way of an example and comparative example.

EXAMPLE

The halogenated silane compound subjected to the decolorizing purification was vinyl trichlorosilane of a lot containing 1.8 ppm of iron and colored in a Gardner color scale (see JIS K 6901) of 12 and APHA (see JIS K 1587) of at least 500. Thus, 482 g of the silane were taken in a glass bottle and admixed with 0.24 g of trimethyl octadecyl ammonium chloride corresponding to 0.05% by weight of the silane compound. The glass bottle was tightly stoppered and shaken at room temperature for 60 minutes. Thereafter, the mixture was filtered to remove the surface active agent from the silane compound which was found to be greatly decolorized to have an APHA value of 40. The content of iron in the thus purified silane compound was 2.2 ppm.

APPLICATION EXAMPLE

The above obtained vinyl trichlorosilane after the decolorizing purification was used as a starting material for the synthesis of an oximesilane compound.

Into a flask of 3 liters capacity equipped with a reflux condenser, stirrer, dropping funnel, thermometer and a gas inlet tube reaching the bottom of the flask were introduced 465 g of methyl ethyl ketoxime and 700 g of anhydrous toluene and 26 g of the decolorized vinyl trichlorosilane obtained in the above example were gradually added dropwise through the dropping funnel into the reaction mixture in the flask kept at a temperature of 55° to 65° C. at a rate of 2.3 g/minute. Prior to, during and after completion of the dropwise addition of the silane compound, ammonia gas was blown into the reaction mixture in the flask through the gas inlet tube at a rate of 1800 ml/minute until 1 hour after completion of the drop-wise addition of the silane compound.

After completion of the reaction in the above described manner, the precipitates of ammonium chloride in the reaction mixture were removed by filtration and the filtrate was distilled at 80° C. under reduced pressure of 5 to 15 mmHg to remove the toluene and unreacted ketoxime compound taking 2 hours. The liquid product left in the flask was analyzed by the gas chromatography to find that the liquid contained 94.4% of vinyl tris(methyl ethyl ketoxime) silane. The liquid had an APHA value of 50.

For comparison, the same procedure as above was repeated excepting the use of vinyl trichlorosilane before the decolorizing purification as the starting material. The liquid after distillation of the reaction mixture contained 94.1% of vinyl tris(methyl ethyl ketoxime) silane and had an APHA value of at least 500 and a Gardner color scale of 10.

COMPARATIVE EXAMPLE

The same experimental procedure as in Example and Application Example was repeated except that the reaction for the synthesis of the oximesilane was undertaken with the vinyl trichlorosilane treated with the cationic surface active agent but without removing the surface active agent by filtration. The reaction mixture after completion of the reaction was subjected to distillation to find that the mixture contained 93.6% of the desired oximesilane compound and was colored in at least 500 by the APHA scale and 0 by the Gardner scale.

What is claimed is:

1. A method for the decolorizing purification of a halogenated silane compound, which is liquid at room temperature, represented by the formula $R^1_{4-a}SiX_a$, in which X is an atom of halogen, $R^1$ is a hydrogen atom or a monovalent hydrocarbon group and the subscript a is 1, 2, 3 or 4, which method comprises the:
   (a) bringing the halogenated silane compound into contact with a cationic surface active agent which is solid at room temperature and insoluble in the halogenated silane compound; and
   (b) separating the halogenated silane compound from the cationic surface active agent.

2. The method for the decolorizing purification of a halogenated silane compound as claimed in claim 1 in which the cationic surface active agent is a quaternary ammonium chloride.

3. The method for the decolorizing purification of a halogenated silane compound as claimed in claim 2 in which the quaternary ammonium chloride is trimethyl actadecyl ammonium chloride.

4. The method for the decolorizing purification of a halogenated silane compound as claimed in claim 1 in which the amount of the cationic surface active agent is in the range from 0.001% to 10% by weight based on the amount of the halogenated silane compound.

5. The method for the decolorizing purification of a halogenated silane compound as claimed in claim 1 in which the halogenated silane compound and the cationic surface active agent are contacted with each other for 2 to 240 minutes at a temperature in the range from 10° to 35° C.

6. The method for the decolorizing purification of a halogenated silane compound of claim 1, wherein $R^1$ are independently methyl, ethyl or vinyl.

7. The method for the decolorizing purification of a halogenated silane compound of claim 1, wherein the halogenated silane compound is tetrachlorosilane, trimethyl chlorosilane, dimethyl dichlorosilane, methyl trichlorosilane, methyl ethyl dichlorosilane, ethyl trichlorosilane, diethyl dichlorosilane, triethyl chlorosilane, n-propyl trichlorosilane, isopropyl trichlorosilane, 2-chloroethyl trichlorosilane, 3-chloropropyl trichlorosilane, vinyl trichlorosilane, vinyl methyl dichlorosilane, propenyl trichlorosilane, allyl trichlorosilane, phenyl trichlorosilane, benzyl trichlorosilane or mixtures thereof.

8. The method for the decolorizing purification of a halogenated silane compound of claim 1, wherein the cationic surface active agent is a salt of a protonated amine, a protonated quaternary ammonium salt, a salt of a protonated carboxylic acid, a salt of a protonated nitrile, a salt of a protonated sulfoxide, a salt of a protonated mercaptan, a salt of a protonated phosphine, a quaternary phosphonium salt or a mixture thereof.

9. The method of claim 8 wherein the cationic surface active agent has 5 to 80 carbon atoms in the cationic part of the salt.

10. The method of claim 8 wherein the cationic surface active agent is tetra(n-butyl) ammonium chloride; tetra(n-hexyl) ammonium chloride; tetra(n-heptyl) ammonium chloride; trimethyl n-nonyl ammonium chloride; n-cetyl trimethyl ammonium chloride; trimethyl octadecyl ammonium chloride or mixtures thereof.

11. The method for the decolorizing purification of a halogenated silane compound of claim 1, wherein the silane compound and the cationic surface active agent are contacted by passing the silane compound through a fixed bed of cationic surface active agent in granular form.

* * * * *